(12) United States Patent
    Strasburger (10) Patent No.: US 10,507,130 B1
(45) Date of Patent: Dec. 17, 2019

(54) SHOULDER AND ARM SUPPORT (71) Applicant: Scott E. Strasburger, Lincoln, NE (US)

(72) Inventor: Scott E. Strasburger, Lincoln, NE (US)

(73) Assignee: PMI 20-90, LLC, Lincoln, NE (US)

( * ) Notice: Subject to any disclaimer, the term of this patent is extended or adjusted under 35 U.S.C. 154(b) by 630 days.

(21) Appl. No.: 15/155,468

(22) Filed: May 16, 2016

(51) Int. Cl.
| A61F 5/00 | (2006.01) |
| A61F 5/37 | (2006.01) |
| A61F 5/01 | (2006.01) |
| A61F 5/058 | (2006.01) |
| A61F 5/34 | (2006.01) |

(52) U.S. Cl.
CPC ............ *A61F 5/3753* (2013.01); *A61F 5/012* (2013.01); *A61F 5/0118* (2013.01); *A61F 5/05858* (2013.01); *A61F 5/34* (2013.01); *A61F 5/373* (2013.01)

(58) Field of Classification Search
CPC ......... A47C 16/00; A47C 20/023; A47C 1/03; A47C 7/68; A47C 7/70; A47C 7/54; A47C 7/543; A47C 7/52; A47C 7/62; A47C 27/18; A47C 27/08; A47C 27/081; A47C 27/14; A47C 20/027; A47C 20/04; A47C 20/048; A61F 5/37; A61F 5/3753; A61F 5/3738; A61F 5/3723; A61F 5/373; A61F 5/0118; A61F 5/012; A61F 5/05858; A61F 5/04; A61F 5/048; A61F 5/042; A61G 7/065; A47G 9/1045; A47G 9/00; A47G 2009/003; A47G 9/10; A47G 9/1009; A47G 2009/1018; A47G 9/1027; A61H 2205/062; A61H 1/0274; A61H 1/0281; A61H 2201/1635; A61H 2201/0103; A61H 2201/1638; A61H 2205/06
See application file for complete search history.

(56) References Cited

U.S. PATENT DOCUMENTS

| 3,324,851 | A | 6/1967 | Posner |
| 8,142,379 | B2 | 3/2012 | Verdonk et al. |
| 8,192,382 | B2 | 6/2012 | Huang et al. |
| 9,259,098 | B2 | 2/2016 | Williams et al. |
| 9,968,477 | B2 * | 5/2018 | Lo .......................... A61F 5/3753 |
| 2005/0229315 | A1 * | 10/2005 | Walpin ................ A47C 20/027 5/633 |
| 2011/0155148 | A1 * | 6/2011 | Golden ............... A61F 5/05841 128/878 |

* cited by examiner

*Primary Examiner* — Victoria J Hicks (57) ABSTRACT

A shoulder and arm support for supporting either the left shoulder and arm or the right shoulder and arm of a patient. The support includes a case which has a shoulder strap secured thereto and a body strap secured thereto. The case has an interior compartment in which a resilient cushion and an air inflatable bladder are positioned. The case includes an outer panel which is pivotally secured to the upper panel of the case and which is pivotally movable between first and second positions. The inflation of the bladder causes the outer panel to be moved from its first position to its second position. The exterior surface of the upper panel has a plurality of arm straps adjustably positioned thereon.

9 Claims, 8 Drawing Sheets

FIG. 8

SHOULDER AND ARM SUPPORT

BACKGROUND OF THE INVENTION

Field of the Invention

This invention relates to a support for treating and protecting the shoulder and arm of a person for numerous orthopedic conditions or following surgery or injury to the area. More particularly, this invention relates to an adjustable support for treating and protecting the shoulder and arm of the person. Even more particularly, this invention relates to an adjustable support which may be used with either the left shoulder and arm of the person or with the right shoulder and arm of the person.

Description of the Related Art

The customary method of supporting the arm and shoulder of a person following an injury or surgery is by using a sling which supports the shoulder against the body in a fixed position. Another option is by using a shoulder abduction pillow or device. Depending on the size of the device, it holds the arm away from the body in a fixed position. The problem with devices of the type described is that they are fixed and not adjustable. Following a shoulder injury or surgery, the position of comfort is extremely variable from patient to patient. Prior art devices are not adjustable to provide support to the arm and shoulder in various attitudes. In the prior art, the fact that the support holds the arm in a fixed position, a significant complication following injury or surgery of the shoulder is the condition adhesive capsulitis (frozen shoulder). The less motion, the greater risk of adhesive capsulitis.

Further, the prior art devices are not able to create continuous passive motion of the shoulder from 20 degrees of abduction to over 90 degrees of abduction.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

The shoulder and arm support of this invention includes a case which is configured to be positioned at either the right side of the patient or the left side of the patient. The case includes an upstanding inner panel having a curved inner side so as to conform to the side of the patient. The case also includes upstanding first and second side panels which extend outwardly from the sides of the inner panel. The case further includes a horizontally disposed bottom panel which is secured to the lower ends of the inner panel and the first and second side panels. The case also includes a horizontally disposed upper panel which is secured to the upper ends of the inner panel, the first side panel and the second side panel. The case further includes an outer panel which has its upper end pivotally secured to the outer end of the end of the upper panel whereby the outer panel is pivotally movable between first and second positions. A flexible bellow is provided which is secured to the outer end of the bottom panel and the outer ends of the first and second side panels. The bellow is also connected to the upper panel.

The inner panel, the first side panel and the second side panel together with the bottom panel define an interior compartment which is closed by the bellow and the outer panel. A resilient foam cushion is positioned in the interior compartment. An inflatable bladder is positioned in the inner compartment outwardly of the outer end of the cushion. The bladder is configured to be moved between a collapsed position and an inflated position. The bladder, upon being moved between its collapsed position and its inflated position, causes the outer panel to be moved from its first position towards its second position.

The exterior surface of the outer panel has a plurality of arm supports secured thereto. The arm supports are adjustably secured to the exterior surface of the outer panel to accommodate different arm sizes and to enable the device to be used to support either the left shoulder and arm or the right shoulder and arm of the patient.

A length adjustable shoulder strap is secured to the first and second side panels of the case and extends therebetween. A length adjustable body strap has its ends secured to the first and second side panels and extends therebetween.

The outer panel, when in its first position, is disposed at about a 20 degree angle with respect to vertical. The outer panel, when in its second position, is disposed in a plane about 90 degrees or more from vertical. The bladder may be inflated to move the outer panel from its first position to its second position or may be used to continuously inflate or deflate the bladder so that the upper panel is continuously moved between its first and second positions to rehab the patient's shoulder.

It is therefore a principal object to provide an improved shoulder and arm support for a patient.

A further object of the invention is to provide a shoulder and arm support which may be used to support either the left shoulder and arm of a patient or the right shoulder and arm of a patient.

A further object of the invention is to provide a shoulder and arm support wherein an outer panel thereof has length adjustable arm supports adjustably secured to the exterior surface of the outer panel.

A further object of the invention is to provide a shoulder and arm support which may create continuous passive motion of the shoulder from 20 degrees of abduction to over 90 degrees of abduction thereby decreasing the risk of adhesive capsulitis and to promote better physiological healing.

A further object of the invention is to provide a shoulder and arm support which may be adjusted in a fixed position for comfort or protection of a surgical repair that is better situated by a certain position.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The numeral 10 refers to the shoulder and arm support of this invention which is designed to be used at either side of a person 12 having a shoulder 14, upper arm 16, lower arm 18 and hand 20.

Support 10 includes body portion or case 22 including a bottom panel 24 having curved inner end 26, a first side 28, a second side 30, and an outer end 32. Case 22 also includes an upstanding first side panel 34 having an upper end 36, a lower end 38, an outer end 40 and an inner end 42. As seen, the outer end 40 of side panel extends downwardly and outwardly from its upper end to its lower end. Case 22 further includes a second side panel 44 having an upper end 46, a lower end 48, and an outer end 50 and an inner end 52. As seen, the outer end 50 of side panel 44 extends downwardly and outwardly from its upper end to its lower end.

Case 22 further includes an outer panel 54 having an upper end 56, a lower end 58, a first side 60 and a second side 62. Side 60 of outer panel 54 is joined to the outer end 40 of side panel 34 by stitching or the like. Side 62 of outer panel 54 is joined to the outer end 50 of side panel 44 by stitching or the like. The lower end 58 of outer panel 54 is joined to the outer end 32 of bottom panel 24 by stitching or the like.

Case 22 also includes a top panel 64 having a curved inner end 66, an outer end 68, a first side 70 and a second side 72. The outer end 68 of top panel 64 is joined to the upper end 56 of outer panel 54 by stitching or the like. Side 70 of top panel 64 is joined to the upper end 36 of side panel 34 by stitching or the like. Side 72 of top panel 64 is joined to the upper end 46 of side panel 44 by stitching or the like.

Case 22 also includes an upstanding curved inner panel 74 which has its upper end secured to the inner end 66 of top panel 64 by stitching or the like and which has its lower end secured to the inner end 26 of bottom panel 24 by stitching or the like. One side of inner panel 74 is secured to the inner end 42 of side panel 34 by stitching or the like and has its other side secured to the inner end 52 of side panel 44 by stitching or the like. The panels 24, 34, 44, 54 and 64 are comprised of a flexible material such as polypropylene. The exterior surfaces of each of the panels 24, 34, 44, 54 and 56 have a fuzzy, loop or fleece structure.

Figure 5:
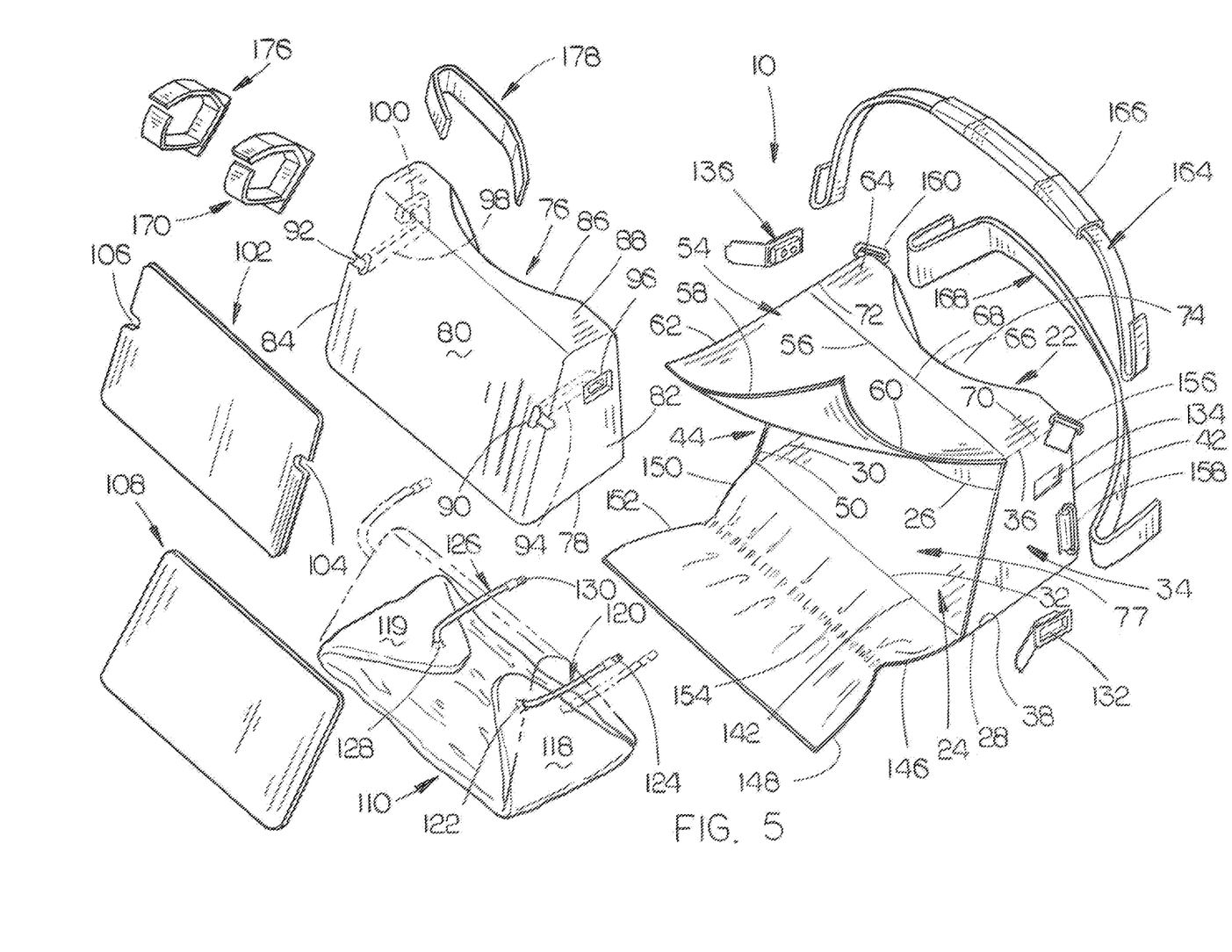
FIG. 5 is an exploded perspective view of the shoulder and arm support of this invention.

The numeral 76 refers to a foam cushion or support which is positioned in the compartment 77 which is defined by the panels 24, 34, 44, 54, 64 and 74. Cushion 76 includes a lower end 78, an outer side 80, a first side 82, a second side 84, a curved inner side 86 and an upper end 88. The outer side 80 of cushion 76 has a pair of notches 90 and 92 formed therein as seen in FIG. 5. Notch 90 is in communication with passageway 94 formed in cushion 76 with the inner end of passageway 94 being in communication with an opening 96 formed in side 82. Notch 92 is in communication with passageway 98 which is in communication with opening 100 formed in side 84 of cushion 76.

A rigid plate 102 is positioned in compartment 77 outwardly of outer side 80 of cushion 76. Plate 102 has notches 104 and 106 formed in the side thereof which register with the notches 90 and 92 respectively of cushion 76. The numeral 108 refers to a rigid plate which is enclosed within outer panel 54 to add rigidity to outer panel 54.

Figure 6:
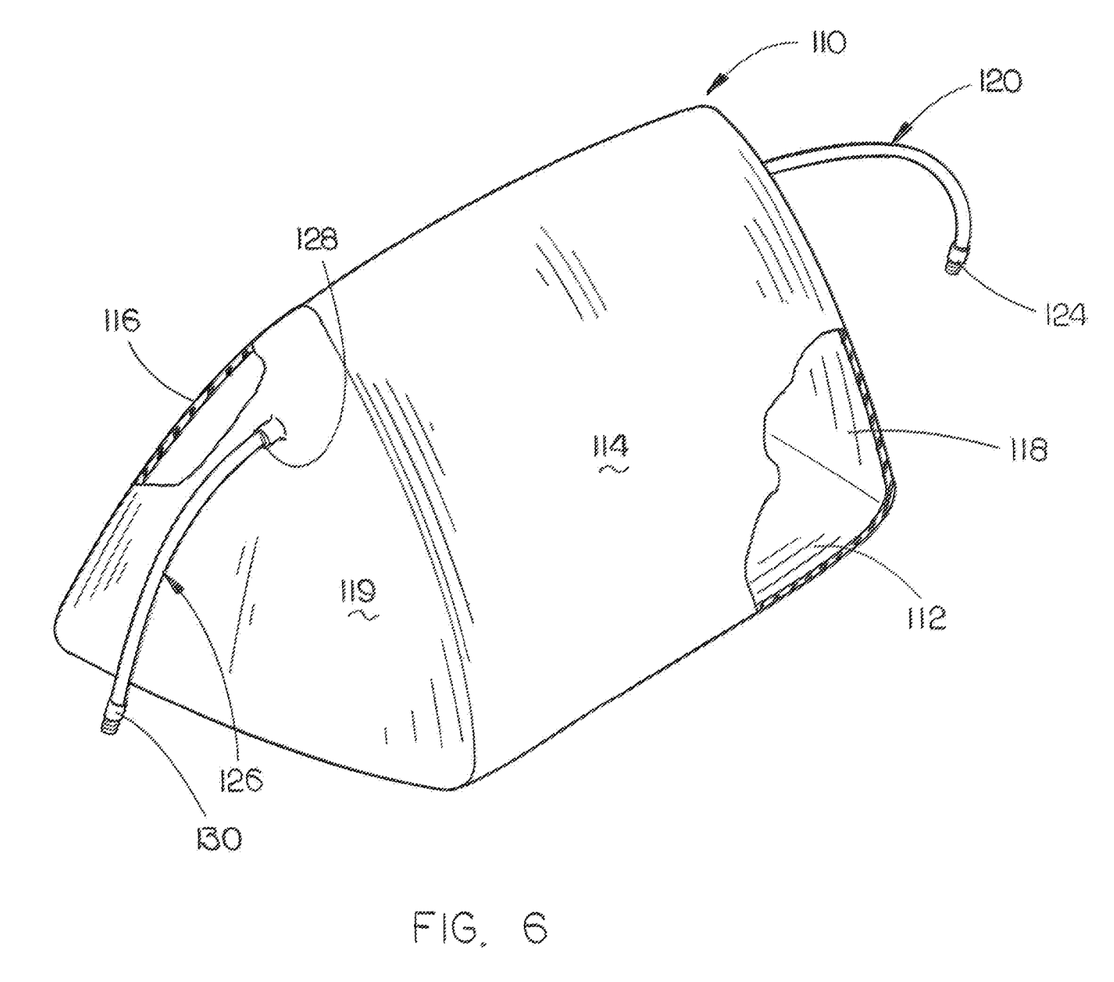
FIG. 6 is a perspective view of the inflatable bladder of this invention with a portion thereof cut-away to more fully illustrate the invention.
Figure 7:
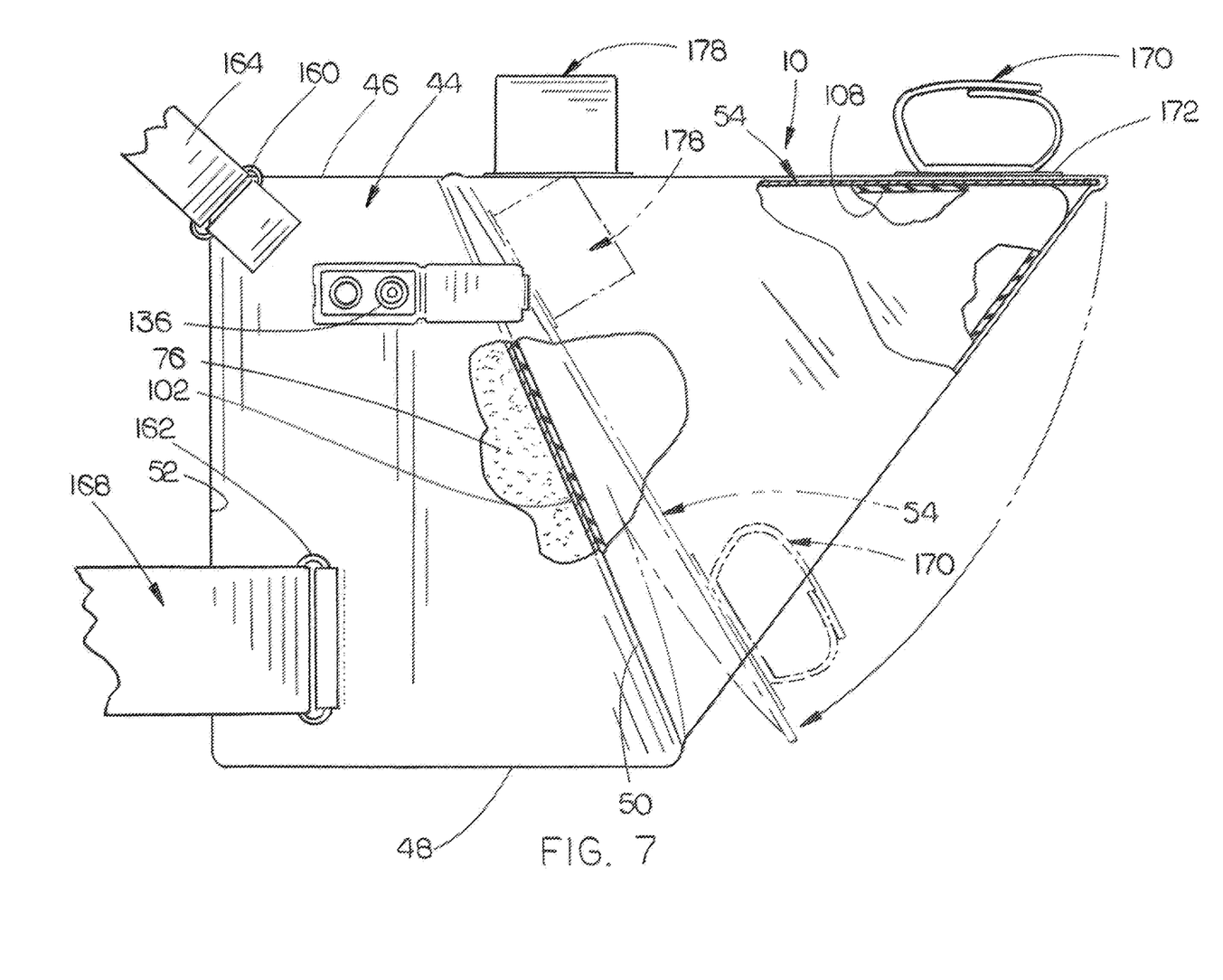
FIG. 7 is a front view of the shoulder and arm support in an elevated position with portions thereof cut-away to more fully illustrate the invention.
Figure 8:
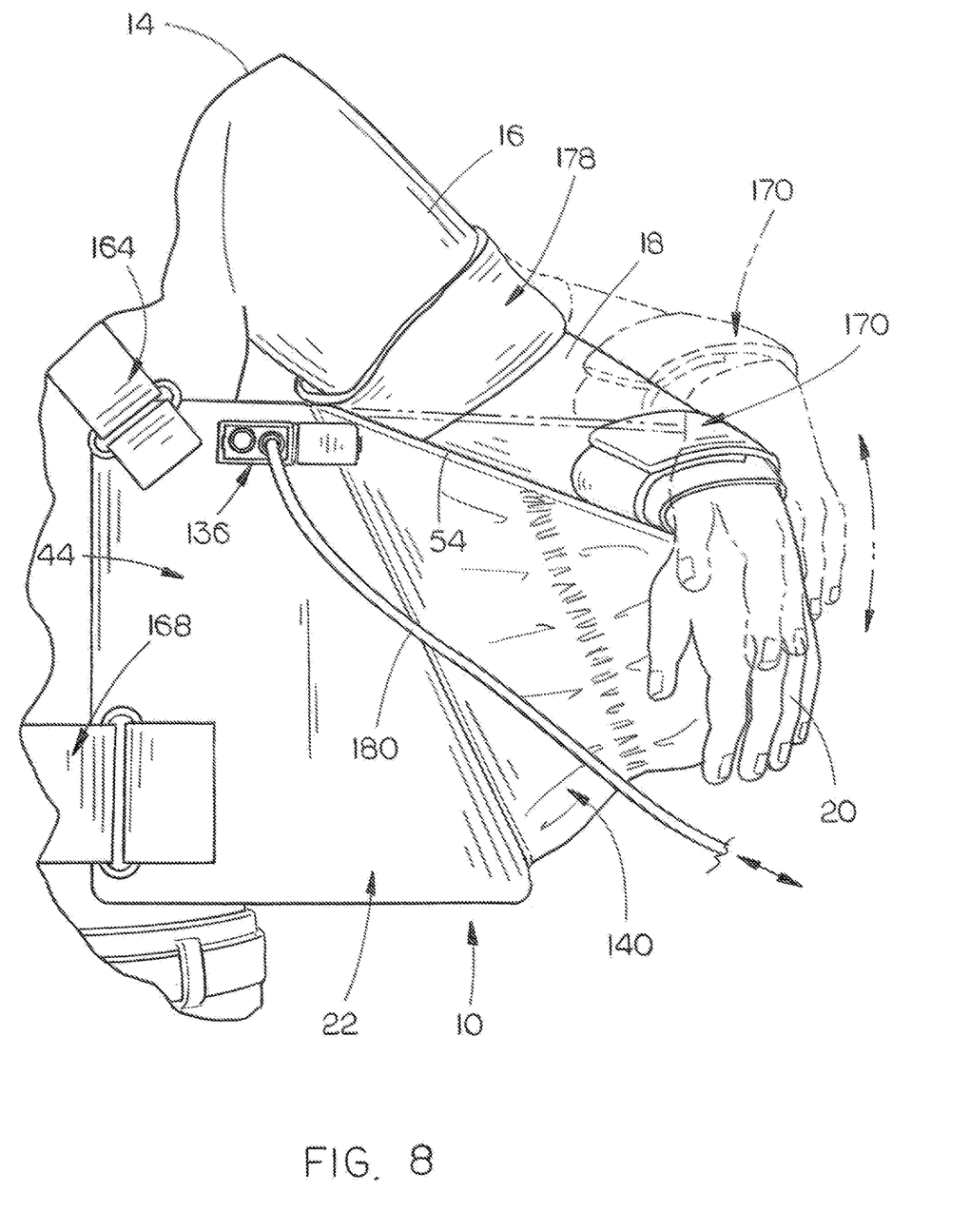
FIG. 8 is a front view of the shoulder and arm support which illustrates the manner in which the arm and shoulder of the patient may be raised and lowered for rehab purposes.

The numeral 110 refers to a plastic or rubber bladder which is movable from a collapsed position as seen in FIG. 5 to a fully inflated position as seen in FIG. 6. Bladder 10 includes a bottom panel 112, an outer panel 114, an inner panel 116, a first side panel 118, and a second side panel 119. A flexible air hose 120 has its inner end 122 in communication with the interior of bladder 110 at side panel 118 and extends therefrom to its outer end 124. A flexible air hose 126 has its inner end 128 in communication with the interior of bladder 110 at side panel 119 and extends therefrom to its outer end 130.

Bladder 110 is positioned in compartment 77 outwardly of the lower end of outer side 80 of cushion 76 when in its collapsed position. The air hose 120 extends through notch 90 in cushion 76, through passageway 94 in cushion 76 and into opening 96 in side 82 of cushion. The air hose 126 extends through notch 92 in cushion 76, through passageway 98 in cushion 76, and into opening 100 in side 84 of cushion 76. An air fitting 132 is positioned in opening 96 in side 82 of cushion and opening 134 formed in side panel 34 of case 22 so as to be in communication with hose 120. An air fitting 136 is positioned in opening 100 in side 84 of cushion and opening 138 formed in side panel 44 of case 22 so as to be in communication with air hose 126.

The numeral 140 refers to a flexible expansion panel or bellow. Panel 140 includes an inner end 142, an outer end 144, side portions 146 and 148 at one side of the panel 140 and side portions 150 and 152 at an opposite side of panel 140. Panel 140 includes at least one elastic band or strap 154 secured thereto by stitching or the like and which extends thereacross as seen in FIG. 5. Inner end 142 of panel 140 is secured to the outer end 32 of bottom panel 24 of case 22 by stitching or the like. Side portion 146 of panel 140 is secured to the outer end 40 of side panel 34 of case 22. Side portion 148 of panel 140 is secured to the first side 60 of outer panel 54 by stitching or the like. The side portion 150 of panel 140 is secured to the outer end 50 of side panel 44 by stitching or the like. Side portion 152 of panel 140 is secured to the second side 62 of outer panel 54 by stitching or the like. The outer end 144 of panel 140 is secured to lower end 58 of outer panel 54 by stitching or the like.

Figure 1:
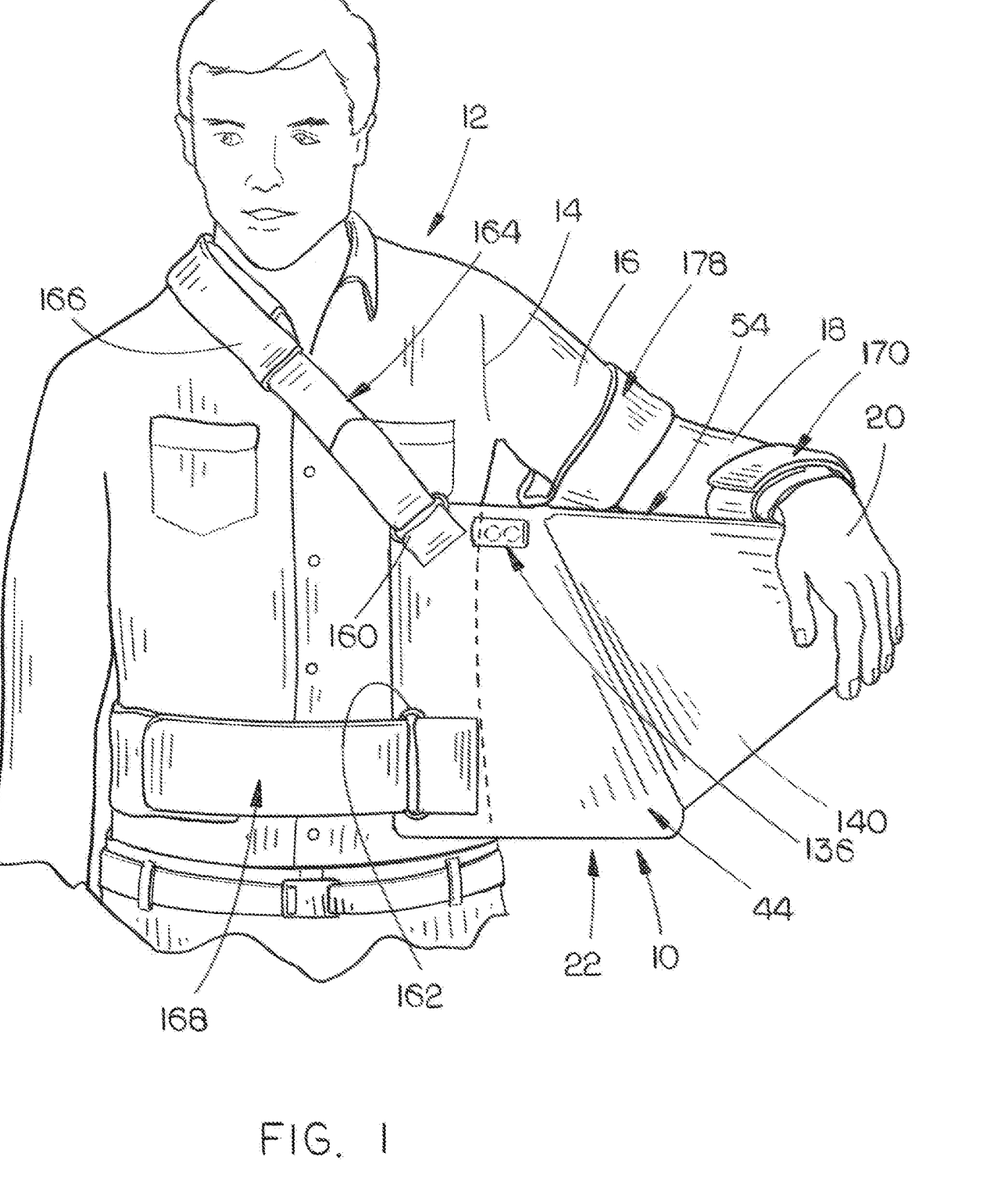
FIG. 1 is a front perspective view illustrating the shoulder and arm support of this invention being secured to the left side of an individual.
Figure 2:
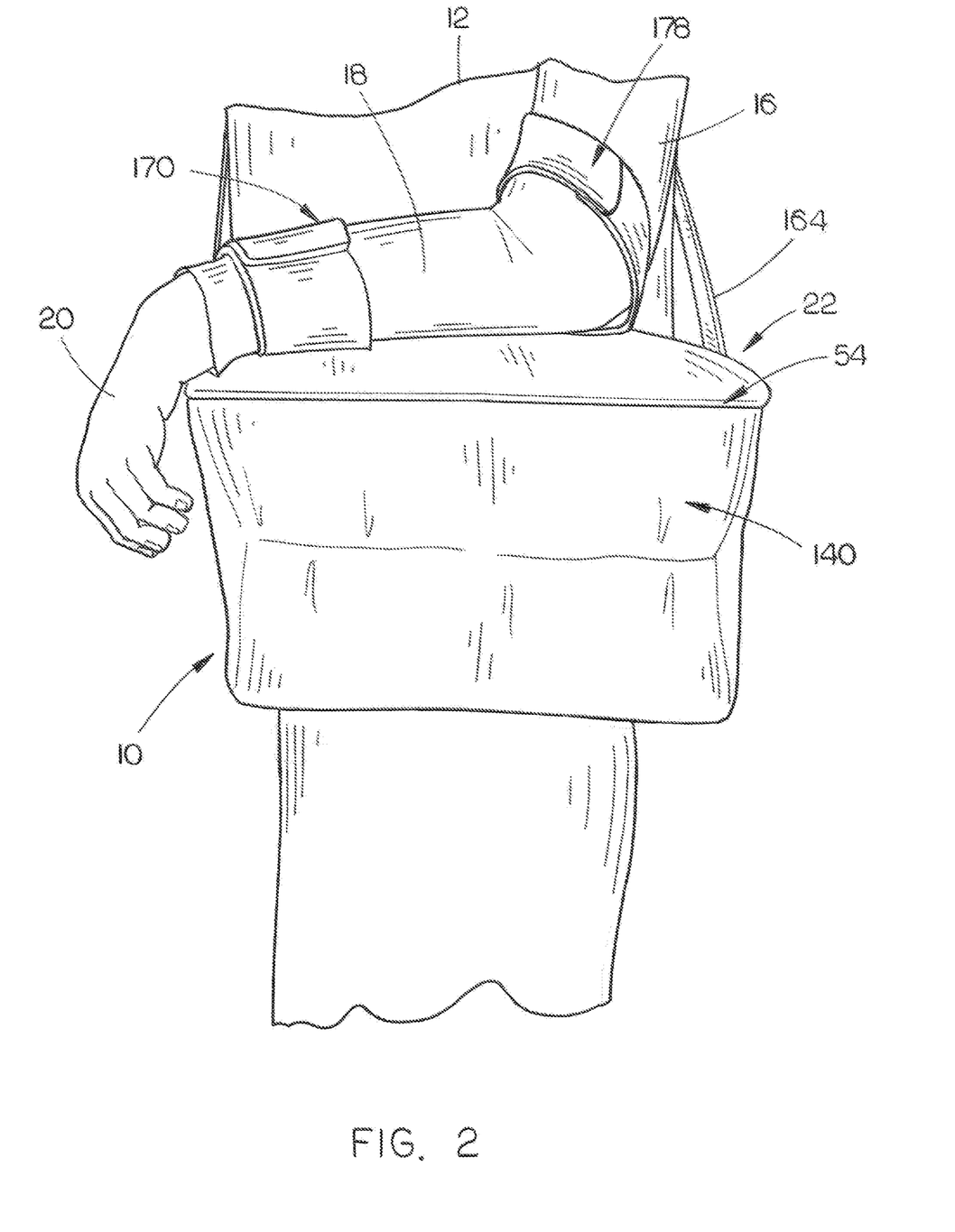
FIG. 2 is a side view of the invention illustrating the arm and shoulder being raised to a particular position.
Figure 3:
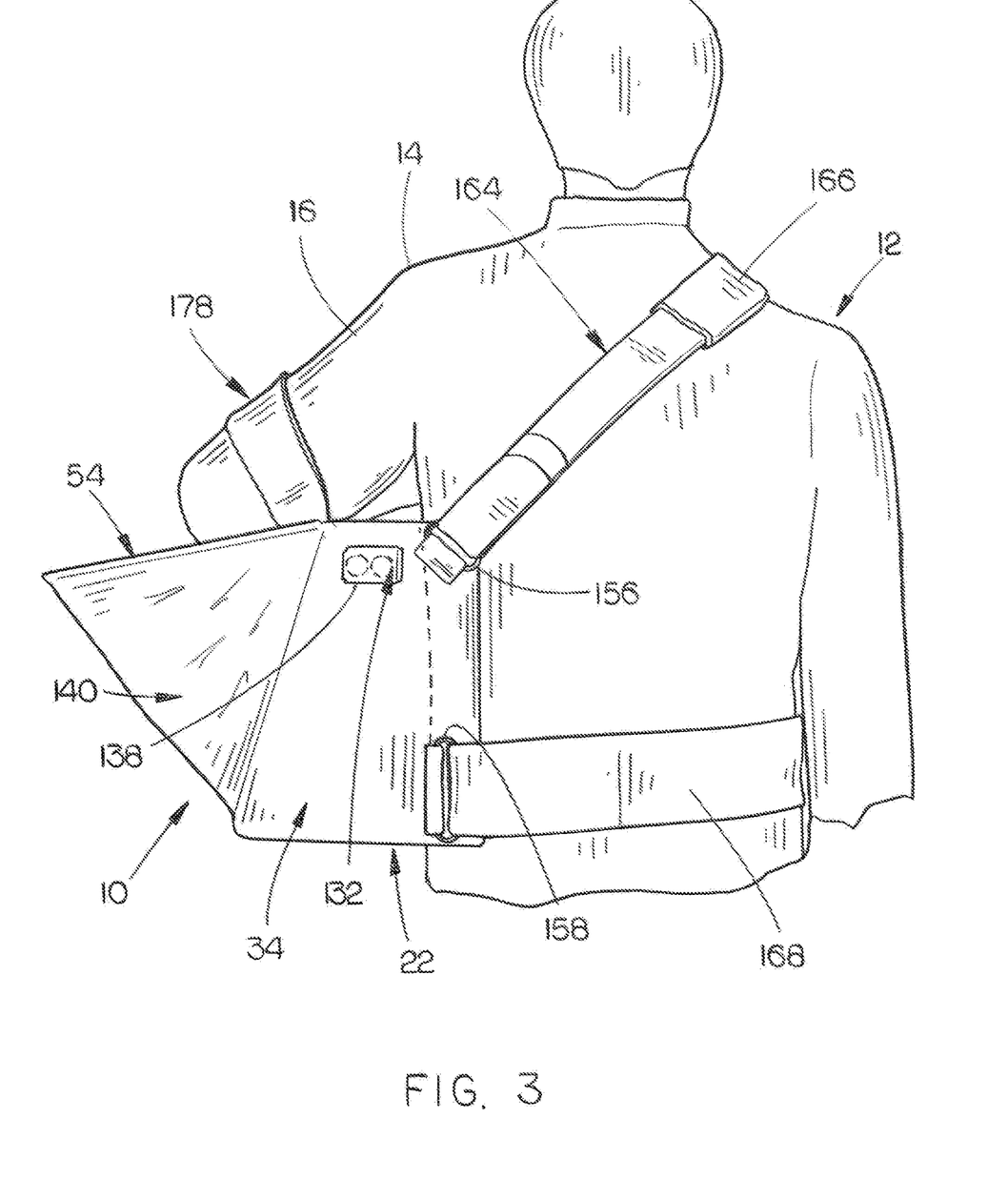
FIG. 3 is a back view of the arm and shoulder support maintaining the arm and shoulder of the patient in a fixed elevated position.
Figure 4:
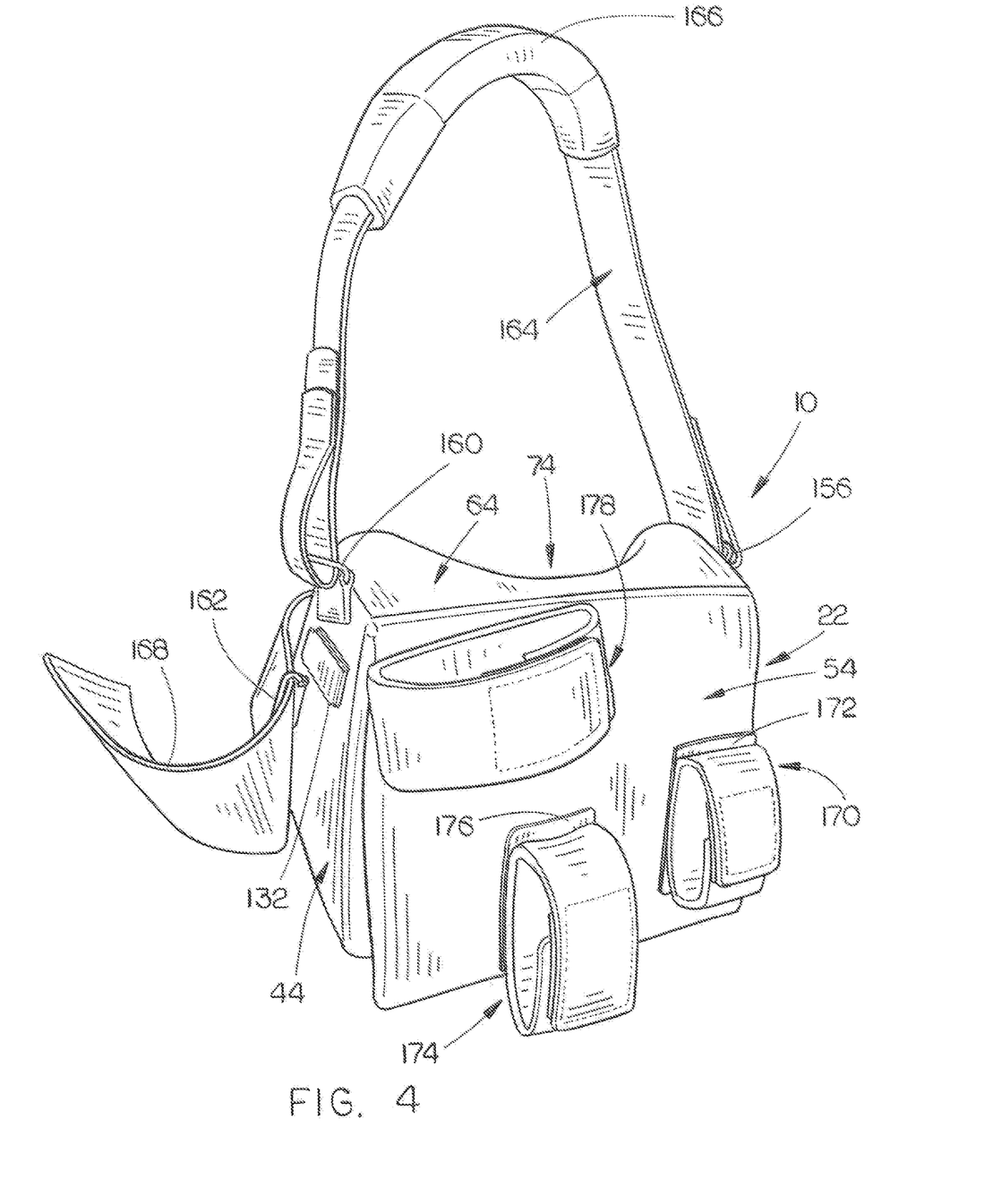
FIG. 4 is a perspective view of the shoulder and arm support of this invention as it would be positioned on the right side of the patient to support the right shoulder and arm of the patient.

Ring connectors 156 and 158 are secured to side panel 34 of case 22 in a spaced-apart manner as seen in FIGS. 4 and 5. Ring connectors 160 and 162 are secured to side panel 44 of case 22 in a spaced-apart manner as seen in FIG. 1.

A length adjustable support strap 164 is secured to and extends between ring connectors 156 and 160 as seen in FIG. 4. An elongated cushion member or pad 166 is mounted on strap 164 as seen in FIGS. 4 and 5. A length adjustable support strap 168 is secured to and extends between ring connectors 158 and 162.

A length adjustable wrist strap 170 is adjustably secured to the exterior side of outer panel 58. Strap 170 includes a strip 172 of hook fastener material which is adjustably secured to the loops or fleece on the exterior side of outer panel 54. A length adjustable lower arm strap 174 is adjustably secured to the exterior side of outer panel 54. Strap 174 includes a strip 176 of hook fastener material which is adjustably secured to the loops or fleece on the exterior side of outer panel 54. A length of adjustable upper arm strap 178 is adjustably secured to the exterior side of outer panel 54. Strap 178 includes a strip of hook fastener material which is adjustably secured to the loops or fleece on the exterior side of the outer panel 54.

The fact that the straps 170, 174 and 178 are length adjustable enables the straps to accommodate different sizes of arms and wrists. An important feature of the adjustable positioning of the straps 170, 174 and 178 is that they enable the support 10 to accommodate either a left arm and shoulder or a right arm and shoulder.

The advantages of the present invention are numerous. First, the instant invention can create continuous passive motion of the shoulder from 20 degrees of abduction to over 90 degrees of abduction thereby decreasing the risk of adhesive capsulitis and to promote better physiological healing. The device of this invention can also be adjusted in a fixed position for comfort or protection of a surgical repair that is better situated by a certain position.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. A device for supporting and treating a patient's shoulder and arm, comprising:
    a case configured to be positioned at one side of the patient;
      said case comprising:
        (a) an upstanding inner panel having an inner side, an outer side, an upper end, a lower end, a first side and a second side;
        (b) said inner side of said upstanding inner panel being curved so as to be capable of conforming to the side of the patient;
        (c) an upstanding first side panel having an upper end, a lower end, an inner end, and an outer end;
        (d) said inner end of said upstanding first side panel being joined to said first side of said upstanding inner panel;
        (e) said outer end of said upstanding first side panel extending downwardly and outwardly from said upper end of said upstanding first side panel to said lower end of said upstanding first side panel;
        (f) an upstanding second side panel having an upper end, a lower end, an inner end, and an outer end;
        (g) said inner end of said upstanding second side panel being joined to said second side of said upstanding inner panel;
        (h) said outer end of said upstanding second side panel extending downwardly and outwardly from said upper end of said upstanding second side panel to said lower end of said upstanding second side panel
        (i) a horizontally disposed bottom panel having an inner end, an outer end, a first side and a second side;
        (j) said inner end of said horizontally disposed bottom panel being joined to said lower end of said upstanding inner panel;
        (k) said first side of said horizontally disposed bottom panel being joined to said lower end of said upstanding first side panel;
        (l) said second side of said horizontally disposed bottom panel being joined to said lower end of said upstanding second side panel;
        (m) a horizontally disposed upper panel having an inner end, an outer end, a first side, a second side;
        (n) said inner end of said horizontally disposed upper panel being joined to said upper end of said upstanding inner panel;
        (o) said first side of said horizontally disposed upper panel being joined to said upper end of said upstanding first side panel;
        (p) said second side of said horizontally disposed upper panel being joined to said upper end of said upstanding second side panel;
        (q) an outer panel having an inner end, an outer end, a first side and a second side;
        (r) said inner end of said outer panel being pivotally joined to said outer end of said horizontally disposed upper panel whereby said outer panel is movable between first and second positions;
        (s) each of said upstanding inner panel, said upstanding first side panel, said upstanding second side panel, said horizontally disposed bottom panel, said horizontally disposed upper panel and said outer panel having interior and exterior surfaces;
        (t) a flexible bellow having an inner end, an outer end, a first side including first and second side portions, and a second side including third and fourth side portions;
        (u) said first side portion being joined to said outer end of said upstanding first side panel;
        (v) said second side portion being joined to said first side of said outer panel;
        (w) said third side portion being joined to said outer end of said upstanding second side panel;
        (x) said fourth side portion being joined to said second side of said outer panel;
        (y) said upstanding inner panel, said upstanding first side panel, said upstanding second side panel and said horizontally disposed bottom panel defining an interior compartment which is closed by said bellow and said outer panel;
        (z) a resilient foam cushion positioned in said interior compartment;

(aa) said resilient foam cushion having an inner end, an outer end, an upper end, a lower end, a first side and a second side;

(bb) an air inflatable bladder positioned in said interior compartment outwardly of said outer end of said resilient foam cushion;

(cc) said air inflatable bladder being configured to be moved between a collapsed position and an inflated position;

(dd) said outer panel is configured to be moved from said first position towards said second position;

(ee) said outer panel having a plurality of arm supports secured to said respective exterior surface;

(ff) a length adjustable shoulder strap having first and second ends;

(gg) said first end of said length adjustable shoulder strap being secured to said upstanding first side panel at said upper end thereof;

(hh) said second end of said length adjustable shoulder strap being secured to said upstanding second side panel at said upper end thereof;

(ii) a length adjustable body strap having first and second ends;

(jj) said first end of said length adjustable body strap being secured to said upstanding first side panel at said lower end thereof; and (kk) said second end of said length adjustable body strap being secured to said upstanding second side panel at said lower end thereof.

2. The device of claim 1 wherein a first air inlet/discharge line extends from one end of said air inflatable bladder with the first air inlet/discharge line being connected to a source of air under pressure configured to inflate or deflate said air inflatable bladder.

3. The device of claim 2 wherein a second air inlet/discharge line extends from a second end of said air inflatable bladder with said second inlet/discharge line being connected to a source of air under pressure configured to inflate and deflate said air inflatable bladder.

4. The device of claim 3 wherein said first air inlet/discharge line may be used when the device is configured to support the left shoulder and arm of a person and wherein said second air inlet/discharge line may be used when the device is being used to support the right shoulder and arm of a person.

5. The device of claim 1 wherein said outer panel has a stiffener plate secured therein.

6. The device of claim 1 may be used to support either the left arm and shoulder or the right arm and shoulder of the patient.

7. The device of claim 1 wherein a plate is positioned at an outer side of said resilient foam cushion.

8. The device of claim 1 wherein said air inflatable bladder has first and second ends and wherein first and second air inlet/discharge lines extend from said first and second ends of said air inflatable bladder respectively to enable the device to be used to support the left shoulder and arm of a person or to support the right shoulder and arm of a person.

9. The device of claim 1 wherein said outer panel is disposed at 20 degrees from vertical when in said first position and wherein said outer panel is disposed at 90 degrees from vertical when in said second position.

* * * * *